United States Patent [19]

Bodine

[11] Patent Number: 5,020,523
[45] Date of Patent: Jun. 4, 1991

[54] FOOT AND LEG SPLINT DEVICE

[75] Inventor: Robert C. Bodine, Mission Viejo, Calif.

[73] Assignee: Capra Resources, Inc., Mission Viejo, Calif.

[21] Appl. No.: 594,842

[22] Filed: Oct. 9, 1990

[51] Int. Cl.$^5$ .......................... A61F 3/00; A61F 5/04; A61F 5/37

[52] U.S. Cl. ............................ 128/80 R; 128/87 R; 128/882

[58] Field of Search .................. 128/82.1, 87 R, 77, 128/155, 156, 157, 165, 882, 90, 89 R, 91 R, 165, 166, 80 R, 80 D

[56] References Cited

U.S. PATENT DOCUMENTS

| 3,548,820 | 12/1970 | Bergen | 128/89 R |
|---|---|---|---|
| 3,800,789 | 4/1974 | Schloss | 128/90 |
| 3,955,565 | 5/1976 | Johnson, Jr. | 128/89 R |
| 3,976,059 | 6/1975 | Lonardo | 128/80 |
| 4,186,738 | 2/1980 | Schleicher | 128/80 R |
| 4,217,893 | 8/1980 | Payton | 128/89 R |
| 4,289,122 | 9/1981 | Mason | 128/89 R |
| 4,401,113 | 8/1983 | Incorvaia | 128/165 |
| 4,454,871 | 6/1984 | Mann | 128/90 |
| 4,505,269 | 3/1985 | Davies | 128/87 R |
| 4,834,078 | 5/1989 | Biedermann | 128/80 R |
| 4,938,777 | 7/1990 | Mason | 128/80 H |

OTHER PUBLICATIONS

AliMed Inc. Product Brochure, 1 page
L'Nard Associates, Inc. Product Brochure, 2 pages
Southpaw Enterprises Catalog Brochure, 3 pages
Sunburst Medical Products Brochure, 2 pages

*Primary Examiner*—Robert A. Hafer
*Assistant Examiner*—Michael Brown
*Attorney, Agent, or Firm*—Stetina and Brunda

[57] ABSTRACT

Disclosed is a device for splinting and immobilizing the lower leg, ankle, and foot of a human being. The device generally includes an L-shaped inner core member having a slightly cupped heel portion, a generally horizontal basal portion extending frontally from the heel portion, and a slightly curved vertical portion extending upwardly from the heel portion. A flexible foam cover is disposed on the core member in a manner as to form a body of the splint device which is positionable against the lower leg, heel, and plantar surface of the foot, the cover being sized and configured to fully conceal the core member therewithin.

10 Claims, 2 Drawing Sheets

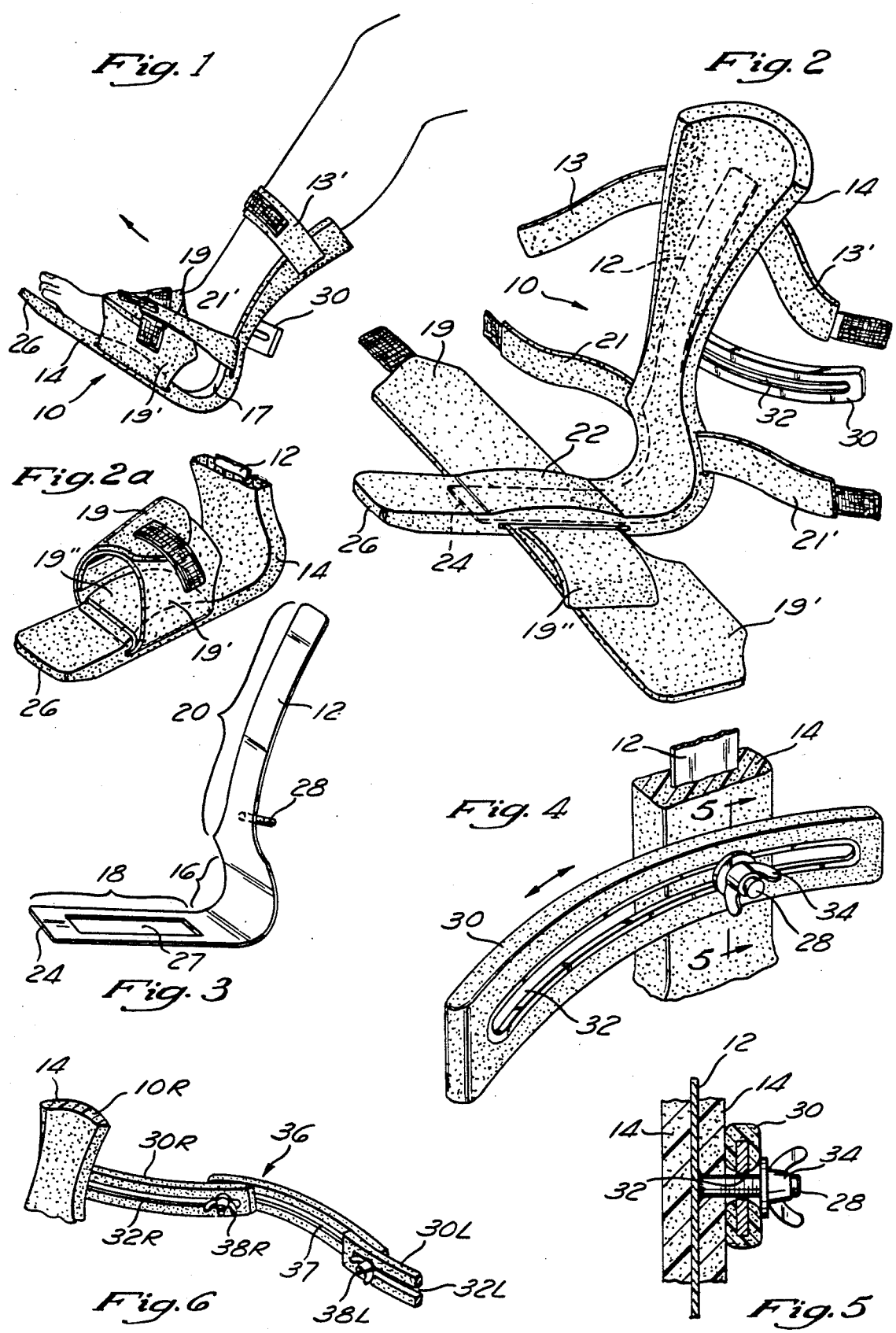

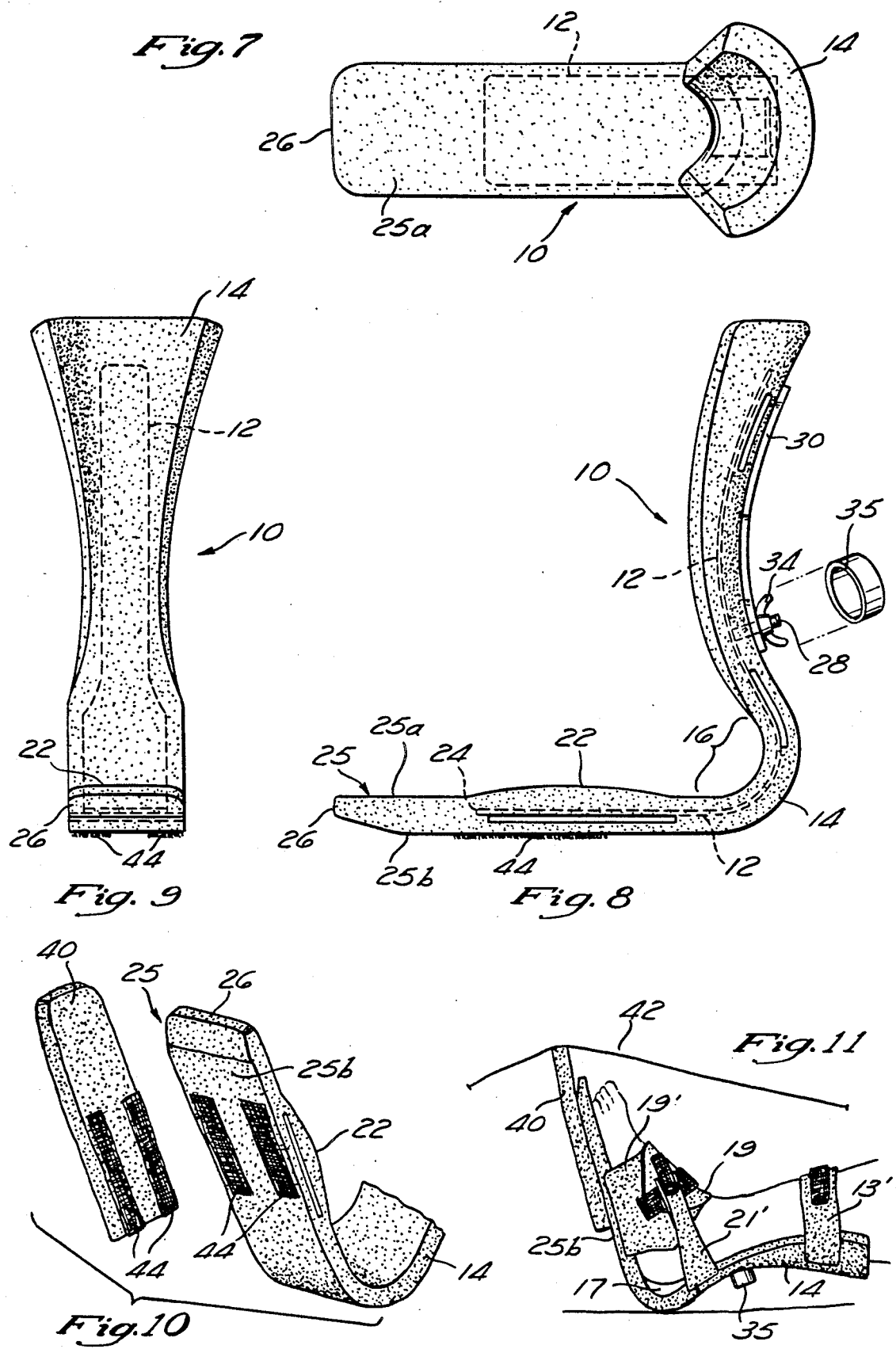

FOOT AND LEG SPLINT DEVICE

FIELD OF THE INVENTION

The present invention pertains generally to medical devices and, more particularly, to a device for splinting and immobilizing the lower leg, ankle, and foot of a human being.

BACKGROUND OF THE INVENTION

The prior art has heretofore included a variety of therapeutic splint devices for maintaining fixed positioning of a patient's foot and/or lower leg. Some of these splint devices have been found to be particularly usable in chronically ill or bedridden patients who are susceptible to a condition known as "drop foot" or "foot drop" wherein the foot hangs in a plantar-flexed position due to neuromuscular atrophy and/or lesions of the peroneal nerve. Drop foot and plantar flexion deformities have been known to develop in patients who spend substantial amounts of time lying in bed with the lower leg/ankle allowed to hang in a flaccid position. Additionally, such plantar flexion deformities are known to develop in patients who have suffered strokes or other debilitating conditions.

One mode of treating and/or preventing plantar flexion deformities of the ankle is to splint or immobilize the ankle of the flaccid leg such that a controlled degree of dorsiflexion of the foot will be maintained. Various splints and splint-like devices have been provided for accomplishing such immobilization of the ankle. Typically, these splints and splint-type devices have comprised generally L-shaped members, attachable to the lower leg and foot so as to hold the foot at an approximate 90-degree angle to the lower leg. Such splints and splint-like devices have included heel guards or heel cushions to prevent the formation of decubitus lesions on the patient's heel. Additionally, some of the prior art splint-like devices have included toe guards which extend forward of the patient's toes so that any bedding positioned over the top of the patient's foot will be held well above the patient's toes so as not to cause undue discomfort or downward pressure on the toes and/or foot. Additionally, some of the prior art devices have been configured so as to be positionable inside a slipper or shoe such that the splint device need not be removed from the patient when it is desired to don a slipper and shoe to permit the patient to sit in a chair or walk about.

In addition to being usable for the prevention and/or treatment of plantar flexion deformities in chronically ill or debilitated patients, foot splints and devices have also been used for various other therapeutic purposes including mobilization of the leg and foot to facilitate healing following traumatic injury and/or surgery.

One example of a prior art foot splint device is found in (LONARDO) U.S. Pat. No. 3,976,059.

Although various foot splints and casts have been known in the prior art, none of these prior art devices are truly optimal for use in all therapeutic situations. Accordingly, there remains a need in the art for a lightweight, lower leg and foot splint device which is fully cushioned or padded, relatively inexpensive to manufacture, and which may be conveniently interconnected by way of a bracket or connector apparatus so as to hold the right and left feet of a patient a given distance apart. Such holding of the right and left feet a given distance apart will help to prevent rolling of the legs from side to side and will also hold the legs a preset distance apart, such that the hips will maintain an adducted positioning, thereby helping to avoid hip abduction deformities as are known to occur in chronically bedridden or debilitated patients.

SUMMARY OF THE INVENTION

In accordance with a preferred embodiment of the present invention, there is provided a foot and leg splint device which comprises a generally L-shaped inner core member having a flexible foam cover disposed thereon. The core member is formed having a cupped heel portion, a generally horizontal basal portion which extends frontally from the heel portion, and a slightly curved vertical portion which extends upwardly from the heel portion. In the preferred embodiment, the flexible foam cover is disposed on the core member in a manner as to form a body of the splint device which is positionable against the lower leg, heel, and plantar surface of the foot. Additionally, the cover is sized and configured to fully conceal the core member therewithin. As can be appreciated, the cover itself defines a base portion corresponding to that part of the foam cover which is disposed about the basal portion of the core member. In this respect, the upper surface of the base portion of the cover includes a support pad formed as an integral portion thereof which is operable to provide for the support of the longitudinal arch of the foot when the splint device is disposed thereon.

The splint device of the present invention further comprises a basal extension member which is attachable to the splint for maintaining blankets in spaced relation to a patient's toes. The basal extension member is attached to the bottom surface of the base portion of the foam cover in a manner whereby the extension member extends upwardly therefrom, above the patient's toes. In the preferred embodiment, VELCRO straps are used to fasten the extension member to the bottom surface of the base portion.

The vertical portion of the inner core member includes a projection extending rearwardly therefrom, wherein the projection extends out of and beyond the outer surface of the foam cover. Additionally, an arcuate stabilizing/connecting bracket is provided for attachment to the splint device. The stabilizing/connecting bracket defines an elongate slot therein which is sized and configured to receive the projection extending from the core member. Advantageously, the stabilizing/connecting bracket serves a dual function. In this regard, the stabilizing/connecting bracket may be utilized as a stabilizing foot or "outrigger" which will rest against an underlying surface to prevent the patient's foot and leg from rolling or turning from side to side. Additionally, the stabilizing/connecting bracket may also be used for purposes of connecting a splint device positioned on the right foot of a patient to a contralateral splint device positioned on the left foot of the patient. In this configuration, a central linking member is used to interconnect the stabilizing/connecting brackets of the splints. Such rigid interconnection between the right and left splint members may be utilized to maintain a desirable degree of hip abduction in bedridden patients.

Further objects and advantages of the invention will become apparent to those skilled in the art upon reading and understanding of the following detailed description of a preferred embodiment and consideration of the accompanying drawings.

BRIEF DESCRIPTION OF THE DRAWINGS

FIG. 1 is a perspective view of a foot and leg splint device of the present invention operatively disposed on the foot and leg of a human subject;

FIG. 2 is a perspective view of a foot and leg splint device of the present invention;

FIG. 2a is a perspective view of a portion of a foot and leg splint device of the present invention;

FIG. 3 is a perspective view of the rigid core insert portion of a foot and leg splint device of the present invention;

FIG. 4 is a rear view of a portion of a foot and leg splint device of the present invention;

FIG. 5 is a sectional view through line 5—5' of FIG. 4;

FIG. 6 is a perspective view showing portions of two (2) foot and leg splint devices of the present invention having connector brackets affixed to one another so as to hold said foot and leg splint devices in lateral juxtaposition with a fixed distance therebetween;

FIG. 7 is a top plan view of a foot and leg splint device of the present invention;

FIG. 8 is a side elevational view of a foot and leg splint device of the present invention;

FIG. 9 is a front elevational view of a foot and leg splint device of the present invention;

FIG. 10 is a perspective view showing the basal portion of a foot and leg splint device of the present invention and a basal extension member which is attachable thereto; and FIG. 11 is a side view showing the preferred use of the basal extension member.

DETAILED DESCRIPTION OF THE PREFERRED EMBODIMENT

The following detailed description and the accompanying drawings are provided for purposes of describing and illustrating a presently preferred embodiment of the invention and are not intended to limit the scope of the invention in any way.

Referring to the drawings, there is provided a foot and leg splint device 10 comprising a generally L-shaped rigid inner core member 12 having a shell 14 of flexible or pliable material, such as flexible plastic foam, disposed thereon. The rigid inner core member 12 is generally L-shaped in configuration and may be formed of a rigid material, including but not limited to aluminum, steel, or various plastics. The heel region 16 of generally L-shaped rigid core member 12 is cupped in a rearward direction to prevent the heel region 16 from routinely making contact with the foot of the patient. A generally horizontal basal portion 18 extends frontally from the heel region 16, while a slightly curved vertical portion 20 extends upwardly therefrom. The soft foam outer cover 14 is disposed on the rigid core member 12 in such manner as to form a body of a splint device 10 which is comfortably positionable against the posterior aspect of the lower leg, heel, and plantar surface of the foot. The portion of foam cover 14 which encases basal portion 18 of core member 12 defines a base portion 25 having an upper surface 25a and a lower surface 25b. An arch support pad 22 is disposed on upper surface 25a to provide for support of the longitudinal arch of the foot when the device 10 is operatively disposed thereon.

The rigid core member 12 is preferably sized so as to be fully concealed within the interior of the foam cover 14. The front edge 24 of the rigid core member 12 terminates some distance behind the front edge 26 of the foam cover 14. The portion of the foam cover 14 which extends frontally beyond the front edge 24 of the rigid core member 12 is flexible enough to permit some degree of bending thereof when the patient's foot is engaged in a walking motion. Additionally, the portion of the foam cover 14 which extends beyond the frontal edge 24 of the rigid core member 12 may be custom out to length to accommodate various sizes of patient's feet. In this preferred embodiment, it is expected that in most applications the practitioner will out the foam cover 14 such that the frontal edge 26 of the foam cover will lie slightly beyond the tip of the patient's toes, as shown in FIG. 1. Such sizing and configuration of the device 10 permits ambulation of the splinted limb without the need for special equipment, custom made slippers, or the like. Finally, the portion of foam cover 14 which covers the heel region 16 of core member 12 is sized to form a space 17 between the foam cover 14 and the heel of the patient when the splint device 10 is disposed on the patient's foot. Space 17 is operable to prevent the formation of decubitus lesions or the like on the patient's heel.

A plurality of strap members are attached to foam cover 14 which are used to secure splint device 10 to the lower leg and foot of the patient. In this respect, upper strap members 13, 13', which are attached to cover 14 at a point near the top of vertical portion 20, are used to secure splint device 10 to the lower leg of the patient in the manner shown in FIG. 1. Similarly, lower strap members 19, 19', which are attached to cover 14 adjacent basal portion 18, are used to secure splint device 10 to the foot of the patient in the manner shown in FIG. 2a. As seen in FIG. 2, a third lower strap member 19" is provided which is used to cover upper surface 25a of cover 14 before a patient's foot is placed thereon. Member 19", which is constructed from an absorbent material, acts as a barrier between a portion of the foot and the underlying foam thereby preventing possible formation of moisture on the surface of the foam and adding to the patient's comfort. A set of intermediate strap members 21, 21' are also provided which are attached to cover 14 adjacent heel portion 16 and are secured to strap members 19, 19' in the manner shown in FIG. 1. Strap members 19, 21, 13 each include VELCRO fasteners attached thereto which are used to interconnect the various strap members, though it will be appreciated that snap connectors or other fastening devices may be utilized as an alternative.

A threaded projection 28 is attached to and extends rearwardly from the back of the rigid core member 12 such that a portion of the projection 28 extends out of and beyond the foam cover 14. Such threaded projection 28 functions as a means for attachment of an optional stabilizing/connecting bracket 30. In the preferred embodiment shown, the stabilizing/connecting bracket 30 comprises a rigid member of metal or plastic covered with foam and having a slightly bowed configuration. An elongate slot 32 extends through the midregion of the stabilizing/connecting bracket 30. The threaded projection 28 is passed through the slot 32 and a wing nut 34 or other retaining nut or apparatus is applied thereto so as to hold the stabilizing/connecting bracket 30 in a desired position on the back side of the splint device 10. As seen in FIG. 8, a cap member 35 is used to cover both projection 28 and wing nut 34, whether or not stabilizing/connecting bracket is attached to projection 28. The stabilizing/connecting bracket 30 serves a dual function. First, such stabilizing-/connecting bracket 30 may be utilized as a stabilizing foot or "outrigger" which will rest firmly against an underlying surface to prevent the patient's foot and leg from rolling or turning from side to side. In those instances when it is desired to use such stabilizing/connecting bracket 30 as a stabilizer or "outrigger", the wing nut 34 will be loosened and the bracket 30 will be slidably moved such that the threaded projection 28 extends through the slot 32 in a manner such that any portion of bracket 30 may extend on either side of the threaded projection 28. The wing nut 34 is then tightened so as to hold the bracket 30 in such position.

The bracket 30 may also be used for purposes of connecting a splint device 10R positioned on the right foot of a patient to a contralateral splint device (not shown) positioned on the left foot of the patient. By such arrangement, the right foot splint device 10R and the left foot splint device (not shown) are incomitently connected to a central linking member 36 by way of brackets 30R and 30L, respectively. As shown in FIG. 6, the preferred method of forming such interconnection is by adjusting brackets 30R and 30L so as to extend medially from each foot splint device 10R and the left foot splint device (not shown) and to firmly secure the brackets 30R and 30L to the respective foot splint devices 10R and the left foot splint device (not shown) by tightening the appropriate wing nuts 34. Thereafter, the central linking member 36 is placed in juxtaposition to the medial-most aspects of the brackets 30R and 30L and appropriate affixation apparatus, such as bolts and wing nuts 38R, 38L, are passed through the slot 37 of central linking member 36, through the respective slots 32R, 32L of the right and left brackets 30R and 30L and sufficiently tightened to hold the brackets 30R and 30L and the central linking member 36 in rigid interconnection. By slidably moving the right and left brackets 30R, 30L in relation to the splint members 10R and the leg foot splint device (not shown) and/or in relation to the central bracket member 36, the practitioner may adjust the angle and distance of separation of the patient's legs. Accordingly, the rigid interconnection between the right and left splint members may be utilized to maintain a desirable degree of hip abduction in bedridden patients.

Referring now to FIGS. 8–10, splint device 10 further comprises a basal extension member 40 which is attachable to the lower surface 25b of foam cover 14. Extension member 40 is attached to lower surface 25b in a manner whereby extension member 40 extends upwardly therefrom, above the patient's toes. In this respect, extension member 40 is operable to maintain covers such as a blanket 42 in spaced relation to the toes, thereby preventing the formation of decubitus lesions or the like on the toes. In the preferred embodiment, hook and loop straps 44, attached to extension member 40 and lower surface 25b, are used to secure extension member 40 to foam cover 14. It will be appreciated however that snap connectors or other fastening devices may be used as an alternative to VELCRO straps 44.

A PREFERRED METHOD OF MANUFACTURE

As can be clearly appreciated from FIGS. 7–9, the presently preferred embodiment of the invention may be manufactured by a foamed-in-place molding process whereby the pliable foam cover 14 is molded or foamed around the rigid core member 12. A slot 27 is formed in basal portion 18 of the rigid core member 12 to allow the foam to flow therethrough, thereby facilitating the even flow of the foam as well as providing for the interconnection of foam cover 14 to the rigid core member 12. It is preferred that the flexible foam cover 14 fully encase or envelope the core member 12 so that no portion of the core member 12 remains exposed and so that the entire exterior surface of the splint 10 is soft and pliable so as to minimize the likelihood of injury to the patient.

The rigid inner core member 12 may be formed of material which is sufficiently bendable to permit bending adjustment of the shape of the splint 10 prior to its application to the human subject. Such rigid inner core member 12 may be placed within a mold and the foam outer portion 14 may be subsequently foamed therearound so as to form the desired encasement or enveloping of the rigid inner core member 12. The thickness of the foam outer portion 14 near the rear side of the splint will be such that the threaded distal end of the projection 28 will extend beyond and out of the foam member so as to provide accessibility and usability of the projection 28 for purposes of attaching the bracket 30 to the splint 10.

What is claimed is:

1. A foot and leg splint device comprising:
   a generally L-shaped inner core member, the inner core member having a heel portion, a generally horizontal basal portion extending frontally from the heel portion, and a generally vertical portion extending upwardly from the heel portion; and
   a flexible foam cover disposed on the inner core member in a manner as to form a body of the splint device which is positionable against the lower leg, heel, and plantar surface of the foot, said flexible foam cover being sized and configured to fully surround the inner core member.

2. The splint device of claim 1 further comprising a basal extension member attachable to the splint for maintaining blankets in spaced relation to a patient's toes.

3. The splint device of claim 2 wherein the cover defines a base portion having an upper surface and a lower surface, the basal extension member being attached to the bottom surface of the base portion in a manner whereby the extension member extends upwardly therefrom above the patient's toes.

4. The splint device of claim 3 wherein hook and loop straps are used to fasten the extension member to the bottom surface of the base portion.

5. The splint device of claim 3 further comprising a support pad disposed on the upper surface of the base portion, the support pad being operable to provide for support of the longitudinal arch of the foot when the splint device is disposed thereon.

6. The splint device of claim 1 wherein the vertical portion of the inner core member includes a projection extending rearwardly therefrom, the projection extending out of and beyond the foam cover.

7. The splint device of claim 6 further comprising an arcuate stabilizing/connecting bracket attachable to the splint device, the stabilizing/connecting bracket defining an elongate slot therein which is sized and configured to receive the projection.

8. The splint device of claim 7 wherein the stabilizing/connecting bracket is adapted to be utilized as a stabilizing foot which will rest firmly against an underlying surface to prevent the patient's foot and leg from rolling from side-to-side.

9. The splint device of claim 7 further comprising a central linking member which is adapted to interconnect the stabilizing/connecting bracket of the splint device to a second stabilizing/connecting bracket of a second splint device in a manner operable to maintain a desirable degree of hip abduction in bedridden patients.

10. The splint device of claim 1 further comprising a plurality of strap members attached to the foam cover, the strap members being operable to attach the splint device to the lower leg and foot of the patient.

* * * * *